United States Patent [19]

Wallace

[11] 4,026,791
[45] May 31, 1977

[54] TREATMENT OF AQUEOUS WASTE

[75] Inventor: James Edward Wallace, Houston, Tex.

[73] Assignee: Pullman Incorporated, Chicago, Ill.

[22] Filed: Oct. 2, 1975

[21] Appl. No.: 618,877

[52] U.S. Cl. .............. 210/21; 260/621 A; 260/627 R
[51] Int. Cl.² .................................. C07C 37/24
[58] Field of Search .......... 208/96, 97; 210/21; 260/621 A, 621 C, 627 R

[56] References Cited

UNITED STATES PATENTS

| | | | |
|---|---|---|---|
| 2,683,752 | 7/1954 | Stanley, Jr. et al. | 260/627 R |
| 2,737,480 | 3/1956 | Adams et al. | 260/621 A |
| 2,807,654 | 9/1957 | Grimmett et al. | 210/21 X |
| 2,812,305 | 11/1957 | Manka | 210/21 |
| 2,824,048 | 2/1958 | Hupe et al. | 260/621 A |
| 2,824,049 | 2/1958 | Maincon et al. | 260/621 A |
| 2,927,075 | 3/1960 | Brown | 210/21 X |
| 3,180,897 | 4/1965 | Sodomann et al. | 260/621 A |
| 3,467,721 | 9/1969 | Bewley | 260/621 A |
| 3,963,610 | 6/1976 | Hauschulz et al. | 210/21 |

*Primary Examiner*—Frank A. Spear, Jr.
*Assistant Examiner*—R. G. Mukai
*Attorney, Agent, or Firm*—Kurt S. Myers; C. W. Crady

[57] ABSTRACT

In the process of producing phenol from cumene, aqueous waste streams result which are contaminated with organic materials, particularly phenol, which are made innocuous to the environment only with substantial difficulty. A process is described to reduce the biological oxygen demand of these aqueous wastes, particularly the phenol content, by a liquid extraction step whereby a highly aromatic fraction of an organic waste stream in the phenol process is used as the solvent. The process includes provision for simultaneous preparation and recovery of the solvent as well as recovery of the phenol.

1 Claim, 2 Drawing Figures

TREATMENT OF AQUEOUS WASTE

BACKGROUND OF THE INVENTION

This invention generally relates to the reduction or organic contaminants and the biological oxygen demand of an aqueous waste stream from a process for producing phenol from cumene.

There are several processes for the production of phenol, in addition to the recovery of phenol from cracked hydrocarbons, but by far the most commercial process involves the cleavage of cumene hydroperoxide into phenol and acetone. Just as in most chemical reactions, by-products are formed contaminating the products and recoverable reactants which must be removed from the system. Even removing the contaminants from the reaction system results in problems, particularly to the environment, since they are disposed of only with significant difficulty. The byproducts and contaminants which are removable as organic materials are typically burned as fuel to provide energy, but aqueous streams containing only small amounts of such contaminants cannot be economically incinerated and cannot be discharged to the environment without considerable treatment.

Previously, the organic contaminants of the aqueous waste streams have been removed by a number of different systems. For instance, in the production of phenol from the catalytic cracking of hydrocarbons, U.S. Pat. No. 3,304,253 describes the use of a light catalytic cycle oil, having a limited content of aromatic materials, as an extractant to remove phenol from a waste water stream. While satisfactory recovery of phenol can be accomplished through the use of many extraneous solvents added to the system or through the use of a product stream in the process, it has not heretofore been recognized that a highly aromatic fraction of an organic waste stream indigenous with the phenol process itself would be useful in lowering the biological oxygen demand of the aqueous waste from the process.

Accordingly, it is an object of this invention to use a fraction of an organic waste stream indigenous to the phenol process to reduce the biological oxygen demand and phenol content of aqueous waste from the process. It is a further object of this invention to use such indigenous waste stream in this manner and still take advantage of the fuel values of such waste stream in ultimate disposal.

SUMMARY OF THE INVENTION

It has been discovered that a solvent obtained by the fractionation of an organic waste stream, which heretofore could only be incinerated for economic and environmentally safe disposal, is useful for treating the aqueous waste from a process for manufacturing phenol from cumene in a multi-stage liquid-liquid extraction step to remove organic materials, particularly phenol, contributing to the biological oxygen demand of the waste water.

The solvent useful for the practice of this invention is obtained by the fractionation of an organic waste stream indigenous to the phenol process. This waste hydrocarbon stream generally includes unrecovered acetone, mesityl oxide, toluene, ethylbenzene, cumene, some methyl styrene and probably other minor constituents. This waste stream is fractionated to separate the solvent fraction, which principally contains aromatic materials such as ethylbenzene, cumene and the like.

The solvent fraction can be recovered from either the hydrocarbon recovery step of the phenol process itself or from the solvent recovery system of the dephenolation process of this invention at a point where the concentration of oxygen-containing organic compounds, such as acetone and mesityl oxide, is a minimum. The light organic materials, i.e., those compounds boiling below the boiling point of the solvent fraction, such as acetone and mesityl oxide, are recovered in an overhead stream. The heavy organic materials, i.e., those compounds with boiling points above that of the solvent fraction, such as alpha methyl styrene and phenol, are recovered as a bottoms stream.

DETAILED DESCRIPTION OF THE INVENTION

Figure 1:
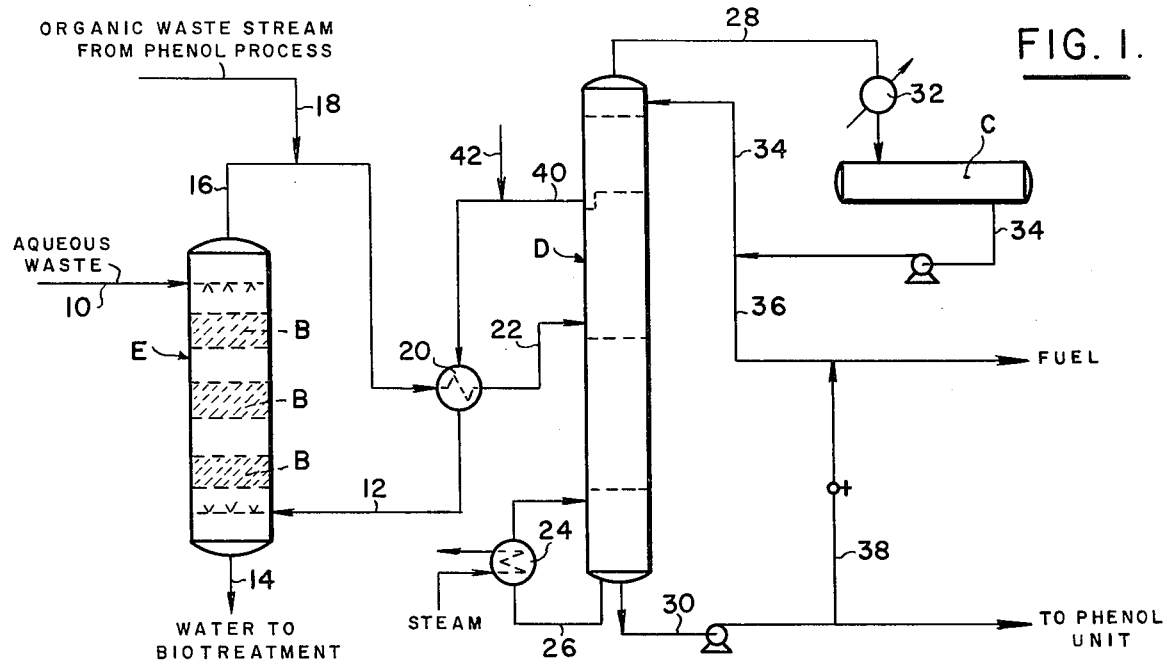
FIG. 1 is a schematic diagram, omitting common fittings, valves and the like, showing the improved method of this invention for reducing the organic contaminants in aqueous waste.

In the operation of the process for the manufacture of phenol from cumene, aqueous wastes containing organic materials are created which require treatment before discharging the water to the environment. Due to the toxic nature of phenol and other organic materials, it is necessary that the waste water streams from the phenol process, including surface water due to rains and washing of apparatus and equipment, must be collected and treated. The quantities of phenol and other organic contaminants vary widely, generally between 2000 ppm and 7000 ppm, but typically can be considered to be an average of about 3500 ppm of the aqueous waste. All of the aqueous waste streams from the process and plant area are preferably collected in a feed tank such that the material fed through the dephenolation process of this invention may be more uniform in the content of organic contaminants.

It has been discovered that a fraction of an organic waste stream indigenous to the phenol process itself is a good solvent for use in a liquid-liquid extraction system of the dephenolation process for removing organic material from the aqueous waste of the phenol process. This solvent is obtained by fractionating the organic waste stream to recover a fraction having a minimum of oxygen-containing compounds and which principally contains aromatic compounds such as toluene, ethylbenzene, cumene and the like. Of course, minor amounts of other hydrocarbons boiling in this range may also be present. The organic waste stream being fractionated to obtain the solvent generally is found in the hydrocarbon recovery section of the phenol process wherein compounds such as cumene and alpha-methyl styrene are recovered and processed for recycling to the phenol process as feed. Previously, this hydrocarbon waste stream was only useful for its heating value as fuel. It has now been discovered that the additional value of extracting the organics from the waste water can be obtained from a portion of this waste fraction and that after such use the hydrocarbons used in the extraction process can still be burned as fuel. Thus, there is no net material cost to the process for obtaining the solvent needed for the reduction of the biological oxygen demand of the aqueous waste. This is a significant improvement over those prior art processes which either involve the use of an externally supplied solvent or the use of a reactant which requires purification prior to use in the phenol process itself.

The solvent thus described has been found to be satisfactory to lower the phenol content of the waste water from the typical value of 3500 ppm to a phenol content of less than a 100 ppm or even less than 1 ppm depending upon the design of the dephenolation process wherein the biological oxygen demand of the aqueous waste stream is reduced.

In the dephenolation process of this invention, the aqueous waste stream is contacted in a liquid-liquid extraction system, preferably an extraction column, with the solvent useful in the practice of this invention. The waste stream can be introduced to the system at substantially ambient temperatures or even higher temperatures as long as the boiling points of any of the substituents in the extraction do not reach their boiling point. It is advantageous however to maintain the temperature as low as possible in order to minimize the solubility of phenol in water. The solvent is preferably introduced into the bottom of an extraction column and flows countecurrent to the aqueous waste stream introduced at the top. The contact by the solvent thus removes phenol and other organic waste materials from the water such as, for example, acetone and mesityl oxide.

The weight ratio of solvent to aqueous materials is preferably kept at about 1:1. However, the ratio may vary from about 0.5:1 to about 3:1. Should the solvent to aqueous materials ratio be at the upper end, i.e., above 3:1, then the capital investment required for an extraction column and solvent recovery system would increase. Depending upon the waste water treatment facilities available, using these solvent ratios, the design of an extraction column can be made following standard engineering concepts such that water exits the extraction column containing from less than about 100 ppm of phenol to less than about 1 ppm.

In the dephenolation process of this invention, the solvent, rich in organics removed from the waste water, leaves the overhead of the extraction system and is fractionated in a column, preferably simultaneously with the organic waste stream from which the solvent used in the practice of this process is obtained. Of course, it is not necessary that the fractionation be simultaneous in the same column to accomplish the results of this invention, but economic advantage is achieved thereby since investment is only necessary for the purchase of a single column system. The single column accomplishes the recovery of solvent used in the extraction, the production of new solvent from the process waste stream, and the recovery of a heavy organics stream containing sufficient phenol to justify the consideration of returning such stream to the phenol process for recovery. The phenol thus returned to the phenol unit for recovery has been separated in the fractionation column from the other organic impurities such as acetone, mesityl oxide, hydroxy acetone, toluene and the like through the distillation.

The overhead stream from the fractionation column containing the light organic materials boiling lower than the solvent can then be used as fuel as before the discovery of this invention. Thus, additional value is achieved without loss of the prior fuel value of the organic waste stream used in the practice of this invention.

A side stream from the fractionation column is removed at the point at which the concentration of oxygen-containing organic material is a minimum. In addition, any toluene that may be present in the column would probably be carried overhead with the oxygen-containing components, such as acetone and mesityl oxide due to the similarity of boiling points of the materials, thus leaving the side stream rich in aromatic compounds such as ethylbenzene and cumene. This side stream is the lean solvent which is introduced in the extraction column to contact the aqueous waste.

The waste organic stream being fractionated to provide the solvent useful in the process of this invention is the stream recovered from the hydrocarbon recovery section of the phenol process. As an alternative to using the entire waste stream from the hydrocarbon recovery section and fractionating it in the column in the dephenolation or waste treatment section, a side stream can be withdrawn from the hydrocarbon recovery column which is roughly equivalent to the stream removed in the fractionating column in the waste treatment section. In the design of a new plant for the production of phenol, it may well be preferable to use this alternative and introduce the solvent stream directly into the bottom of the extraction column, either as separate streams or cojoint, with the lean solvent recovered in the dephenolation section.

To more specifically describe the method of this invention, with particular reference to FIG. 1, aqueous waste containing organic contaminants enters the dephenolation system through a conduit 10 to enter the top of a liquid-liquid extraction vessel E. The extraction column E has one or more theoretical stage(s), or transfer unit(s), for the extraction. The drawing illustrates a column having three beds B of packing material.

The solvent useful in the practice of this invention is fed into an extraction column E through line 12 and moves up through the beds of the column in countercurrent flow to the organic containing aqueous waste. The extractant, or treated water, is removed from the extraction column E through line 14 to be discharged, usually after biological treatment, to the environment. The water thus treated within this extraction column in the process of this invention using the solvent fraction cut from the organic waste stream indigneous to the phenol process employed in the process of this invention has most of the organic matter removed. The system can be engineered to have a phenol content of less than about 100 ppm or even as low as less than 1 ppm depending upon the requirements of the individual situation. Heretofore such low levels of phenol content in waste water from the phenol process could only be obtainable through use of less economic solvents which required additional recovery techniques.

From the extraction column E, the rich solvent is recovered overhead through line 16. The solvent is rich in the organic materials removed from the aqueous waste such as the phenol, acetone, mesityl oxide and other incidental organic contaminants. Should the entire overhead stream from the hydrocarbon recovery section of the phenol process be used to provide the make-up solvent for the removal of the organics from the liquid waste, it is preferably introduced into the line 16 through line 18 and proceeds in admixture with the rich solvent stream 16 from the extraction column E through heat exchanger 20 where it is heated to a proper temperature for use as the feed for distillation. The ratio of the make-up solvent to the solvent stream 16 from the extraction column E is dependant upon the amount of waste hydrocarbon produced from the phenol unit. Typically, this ratio may vary between 1:10 and about 1:30.

The heated phenol-rich solvent stream exits heat exchanger 20 through line 22 and thence into distillation column D. The distillation column D is fitted with a reboiler heated by steam through a heat exchanger 24 by recycling the bottoms stream from the column D through line 26 and returning it to the column in the manner well-known to the skilled engineer. It is preferable that the distillation column D be a multiple plate column which allows the efficient removal of a side stream since it is very important in the successful practice of the method of this invention that a side stream be removed at the point where the concentration of oxygen-containing organic waste, such as acetone and mesityl oxide are a minimum.

The design of the distillation column D is a function of capital and energy costs, availability of the organic waste stream from the phenol process and the desired effluent water quality. Though wider ranges can be used, a reflux to feed ratio of between about 0.5:1.0 and about 3.0:1.0 is adequate to meet the quality considerations of the lean solvent when a column of from about 15 to about 45 trays is used. While these numbers can vary somewhat according to specific situations, the skilled engineer would have no difficulty in adjusting the design to the particular situation. The number of trays between the feed inlet 22 and the side stream from which the solvent fraction is removed should be at least about five trays and preferably about ten.

Preferably, the distillation column D is operated with the feed, either the solvent rich in organics from the extractor E or a mixture of the rich solvent from the extractor E and the stream from the hydrocarbon recovery section of the phenol process (FIG. 2) entering through line 22. This provides for the removal of the light organic materials which boil below the boiling point of the useful solvent and contain components such as mesityl oxide, acetone, toluene, ethylbenzene and the like overhead through line 28 while heavy organic materials boiling above the boiling range of most of the solvent, including the phenol, are recovered as a bottoms stream of the distillation column D through line 30.

The light organic materials, as defined above, exiting the column D through line 28 pass through heat exchanger 32 and to condenser C where they are condensed to the liquid form, exiting the condenser C through line 34 through which a portion of the material is returned to the column D as a reflux stream. A portion of the organic contaminants making up this overhead stream are purged from the system through line 36 and are disposed of by incineration for use as fuel. Thus, the heating value of the organic waste stream of the phenol process is preserved and utilized. The bottoms stream of heavy organic materials exiting the column D through line 30 is rich in phenol and may have a phenol concentration as high as about 20% indicating a significant recovery of product. This material may be returned through line 30 to the phenol unit for product recovery or may be purged through line 38 to be incinerated as fuel with the overhead stream containing light organic material from the system.

With respect to the solvent useful in the process of this invention, it exits the distillation column D as a side stream cut through line 40. The positioning of the side stream can be readily calculated by a competent engineer such that the lean solvent composition exiting the column D through line 40 will have a minimum concentration of oxygen-containing contaminants.

The lean solvent stream useful in the practice of the process of this invention generally consists essentially of the aromatic compounds ethylbenzene and cumene, for example. Even though some oxygen-containing compounds may be present, it is desirable to reduce the content of these compounds as much as is practically possible, since the oxygen-containing contaminants found in the phenol process have a greater solubility in water than the aromatic compounds and thus reduce the overall effectiveness of the solvent in lowering the phenol and B.O.D. content of the waste water. Minimizing the oxygen-containing compounds assures that the maximum removal of organic contaminants is accomplished in the extraction column E. Typically in the treatment of the aqueous stream from the phenol process using cumene as the reactant, the lean solvent stream will be rich in ethylbenzene and contain cumene, probably some toluene, and possibly minor amounts of other hydrocarbon materials which do not substantially affect the solvent capability in the practice of this invention.

The stream 40 containing the solvent passes through heat exchanger 20 where it supplies heat to the feed going to the column D. From the exchanger 20 the solvent passes through line 12 to the extraction column E where it contacts, in multi-unit countercurrent flow, the aqueous contaminated waste from the phenol process. Should the solvent-containing side stream be taken from the hydrocarbon recovery section of the phenol unit, the make-up solvent would preferably be introduced through line 42 into line 40. It could also be optionally introduced into line 12 or the column E directly, depending upon sound engineering considerations.

Figure 2:
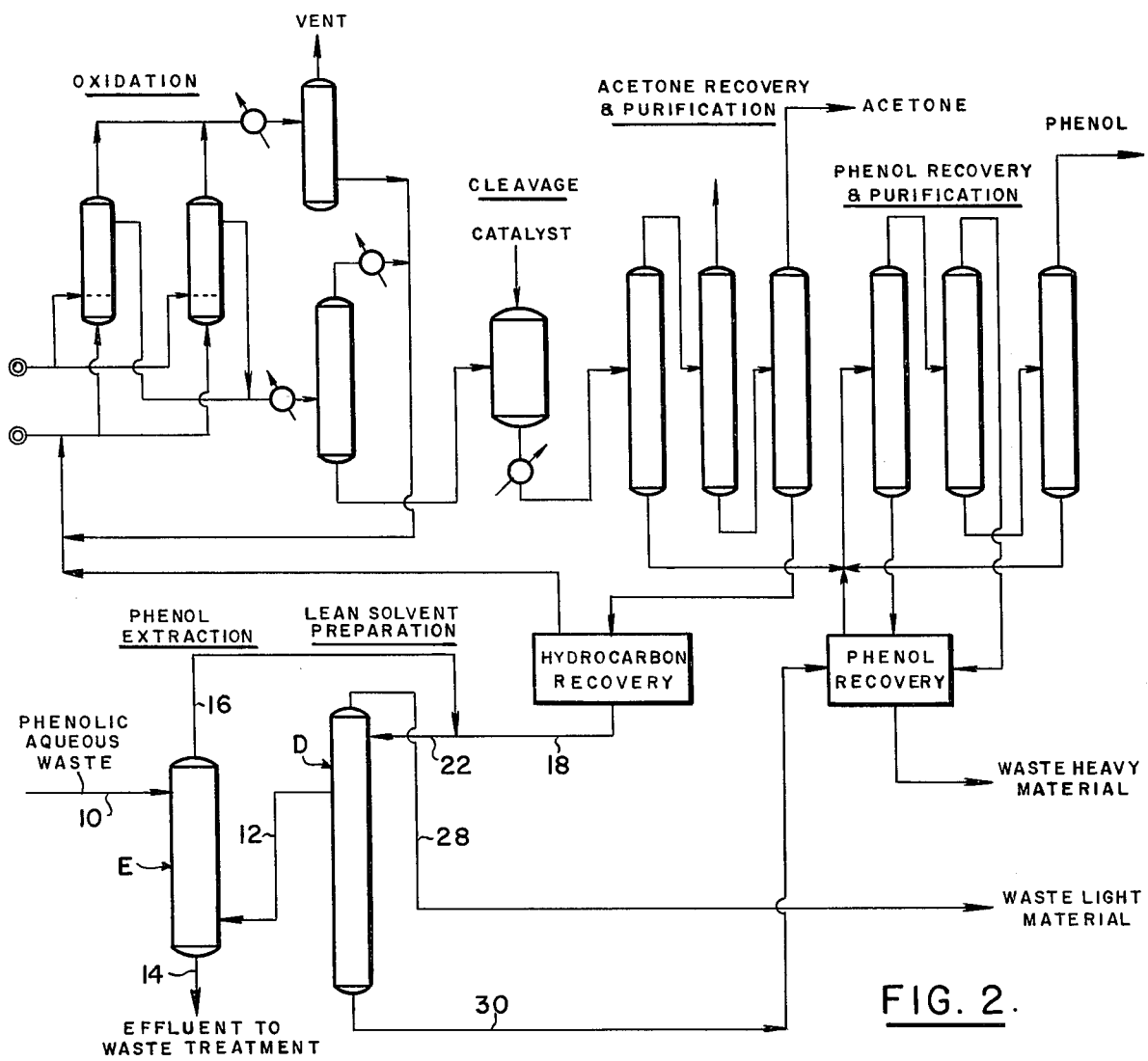
FIG. 2 is a schematic diagram, omitting common fittings, valves and the like, showing the improved method of this invention in conjunction with a well-known process for the manufacture of phenol from cumene.

Turning now to FIG. 2 which shows the schematic diagram of the process of this invention more particularly described above and shown in FIG. 1 as it is integrated into the overall well-known process for the manufacture of phenol and acetone by oxidation of cumene. The numbers used in FIG. 1 are repeated for FIG. 2 for the same elements. Since the process for the manufacture of acetone and phenol is well-known and the flow diagram of said process is shown along with a brief description thereof in the November, 1971, issue of *Hydrocarbon Processing Magazine* at page 187, no detailed discussion will be made of such process. However, it is pointed out that the solvent from the organic waste stream indigenous to the phenol process leaves the hydrocarbon recovery section of the process through line 18 and is charged to the distillation column D through line 22 just as described above with respect to the detailed description of FIG. 1 of the process of this invention. As also described above, the solvent can be fractionated from the organic waste stream indigenous to the process within the hydrocarbon recovery zone and be charged directly to the extraction column E or intermixed with the feed line 12 to the extraction column E carrying the lean solvent. It is also to be noted that the bottoms stream 30 from the distillation column D having the heavy organic materials, as that term is hereinbefore defined, from the solvent recovery distillation in the column D is shown being returned through line 30 to the phenol recovery section of the process. Thus, it is seen that the process of this invention uses a waste stream from the phenol process itself to great advantage in removing organic materials from the aqueous liquid waste discharged from the extraction column E through line 14 to the environment. The process of this invention also gives the advantage of returning to the phenol process the values recovered both in the form of recovered phenol and the fuel value of the light organic materials removed from the column D as an overhead stream through line 28.

Of course, one of ordinary skill in the art may make obvious modifications of the parameters described and the equipment used without departing from the scope and spirit of this invention as set forth in the appended claims.

I claim:

1. In a process for producing phenol from cumene, an improved method for preparing a lean solvent for reducing the biological oxygen demand and phenol content of aqueous waste contaminated with organic materials from the process by liquid-liquid extraction, which comprises the steps of:
   a. fractionating in a single column a mixture of a organic waste stream indigenous to the phenol process boiling between alpha-methyl styrene and acetone and the rich solvent stream from the extraction of said aqueous waste;
   b. recovering (1) a side stream lean solvent cut which principally contains ethylbenzene and cumene substantially free of oxygen-containing organic compounds, (2) an overhead stream containing light organic materials and (3) a bottoms stream containing heavy organic materials including phenol; and
   c. contacting said aqueous waste in an extraction system with said lean solvent cut from (1).

* * * * *